United States Patent [19]

Daneshvar

[11] Patent Number: 5,423,852
[45] Date of Patent: Jun. 13, 1995

[54] DEVICE FOR PREVENTING POST-CATHETERIZATION WOUND BLEEDING

[76] Inventor: Yousef Daneshvar, 21459 Woodfarm, Northville, Mich. 48167

[21] Appl. No.: 989,825

[22] Filed: Dec. 14, 1992

Related U.S. Application Data

[63] Continuation-in-part of Ser. No. 800,085, Nov. 29, 1991, Pat. No. 5,263,966.

[51] Int. Cl.$^6$ ............................................. A61B 17/12
[52] U.S. Cl. ......................................... 606/201; 602/53; 602/61; 128/118.1
[58] Field of Search ................. 606/112, 201–204; 128/118.1, 98.1, 96.1; 602/13, 67, 53, 61

[56] References Cited

U.S. PATENT DOCUMENTS

| | | | |
|---|---|---|---|
| 2,493,406 | 1/1950 | Hicks | 128/118.1 X |
| 3,171,410 | 3/1965 | Towle et al. | 128/118.1 X |
| 4,135,503 | 1/1979 | Romano | 128/118.1 X |
| 4,622,957 | 11/1986 | Curlee | 128/118.1 |
| 4,671,264 | 6/1987 | Frangi | 128/96.1 |
| 4,957,105 | 9/1990 | Kurth | 128/96.1 |
| 4,977,893 | 12/1990 | Hunt | 128/96.1 X |
| 5,170,781 | 12/1992 | Loomis | 128/118.1 |

FOREIGN PATENT DOCUMENTS

| | | | |
|---|---|---|---|
| 910340 | 6/1946 | France | 128/118.1 |
| 2649314 | 4/1991 | France | 128/96.1 |
| 821824 | 11/1951 | Germany | 128/118.1 |
| 45062 | 7/1908 | Switzerland | 128/118.1 |
| 4383 | of 1880 | United Kingdom | 128/118.1 |
| 9011744 | 10/1990 | WIPO | 606/202 |

Primary Examiner—Michael H. Thaler

[57] ABSTRACT

Bleeding from a wound created as a consequence of catheterization of a vessel proximate the groin is prevented by a balloon that is secured by means of a wrap around the abdomen and thigh, and inflated. Several embodiments are disclosed. In one, the balloon has an edge proximate to and parallel with the groin line; in another, there are two such balloons on opposite sides of the groin line; in a third, a third balloon wedges the first two. The balloons may be attached to the insides of shorts. Electrodes placed over the area can detect bleeding.

4 Claims, 14 Drawing Sheets

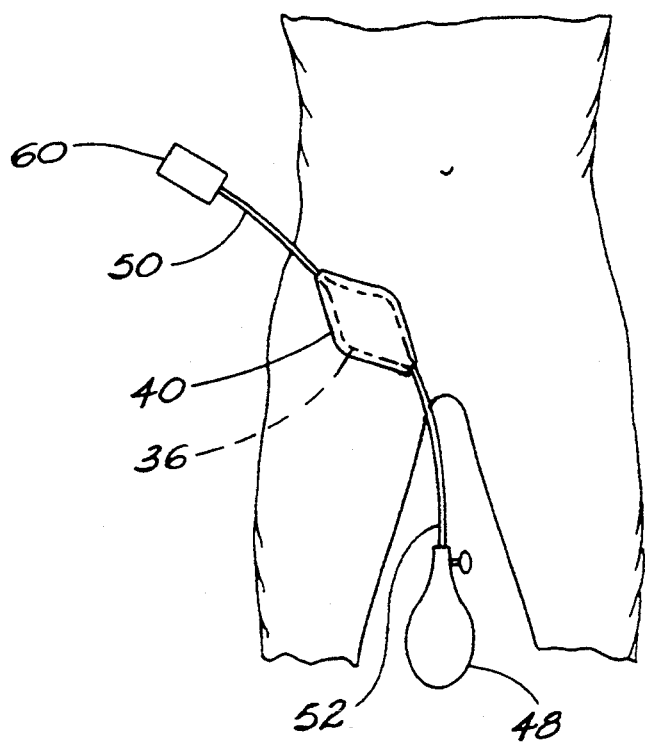
Fig. 5
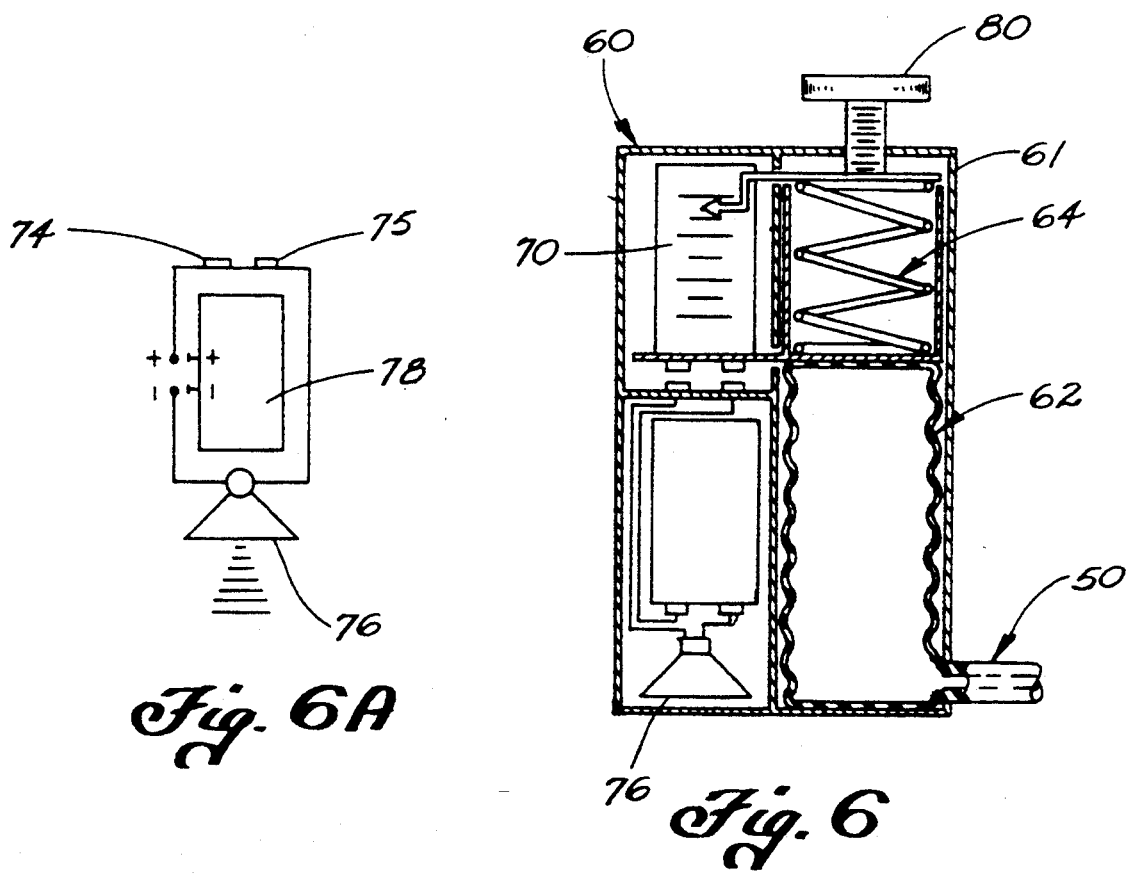
Fig. 6A
Fig. 6

DEVICE FOR PREVENTING POST-CATHETERIZATION WOUND BLEEDING

REFERENCE TO A RELATED APPLICATION

This application is a continuation-in-part of my allowed application Ser. No. 07/800,085, filed Nov. 29, 1991, now U.S. Pat. No. 5,263,966.

FIELD OF THE INVENTION

This invention relates to the post-catheterization prevention of bleeding from a wound created as a consequence of inserting a catheter, or other similar device, into a vessel. More particularly, it relates to preventing bleeding from a wound proximate a person's groin.

BACKGROUND AND SUMMARY OF THE INVENTION

One of the common concerns in cardiac catheterization and related interventions is the problem of bleeding after catheterization of a vessel. This well known and familiar problem may even need corrective surgery in extreme cases.

A commonly used method of preventing such complication is quite primitive, and may be ineffective in some instances. That method is to position a sand bag in the area over a pressure bandage. In general, it may be considered a rather crude and uncomfortable method since, 1) it does not apply an appropriate amount of pressure all the time, 2) the sand bag may slide and/or fall, 3) the patient must be kept practically motionless to avoid dislocation of the sand bag, and 4) the patient is usually told not to raise the head over 15 degrees. Insofar as the applicant is aware, no other method has replaced the sand bag to any significant degree.

This problem has led to the applicant's creation of a much better alternative, which the applicant has named the D. Device. This device affords much easier use, gives much better pressure control, and is more comfortable for the patient. Not only can the patient move more, but it is believed that he/she may be discharged earlier from the hospital.

Briefly, the device is designed to prevent bleeding after catheterization of a groin vessel in connection with any of a number of different interventions, such as angiography for the heart, brain, arteries, etc., during which a vessel, such as an artery, has to be entered for diagnostic or treatment purposes. Naturally, the resulting wound has tendency to bleed.

The device comprises a main wrap, made preferably from tough synthetic fabric, which wraps around both the lower abdomen and the upper thighs to give support for the application of pressure to the groin by a specially shaped inflatable balloon contained within the wrap. The pressure inside the balloon can be monitored by a gauge, which can also have a safety alarm to indicate if the pressure inside the balloon drops. Another wrap, made preferably from a thin layer of non-irritating, soft, disposable material matching the shape of the main wrap may cover the skin under the main wrap to prevent contamination. Means are also provided so that bleeding which may occur after the device has been placed on the person can be seen by an observer.

I have also noticed that the anxiety of patients from bleeding after catheterization is real and well founded; they get very concerned about the development of bleeding and even minimal expansion in their arteries. I have heard from my own patients about their fear that with movement, their artery may open and bleed. These reactions, as well as worries of people with hernia, made me believe that there is a need for better protection and assurance of patients from bleeding and complications after cardiac catheterization and related interventions. This thought, as well as my own concern about patients' well being, have resulted in a modification and improvement in my previous device. This improvement will be used to protect a patient when he or she is ready to be discharged from the hospital or cardiac catheterization lab clinic. It also provides peace of mind to patients, their relatives, and the physician. Also, the anxiety and concern of patients with hernia have resulted in modification of this unit to allow it to be very beneficial in patients with hernia or similar problems.

This improvement invention comprises a unit that has a pressurized balloon that is held in place by straps, wraps, or shorts, to prevent bleeding and related complications in the groin area after cardiac catheterization or similar procedures. The unit is also very beneficial in patients with hernia or similar problems by applying pressure in front of a hernia to prevent its expansion related problems.

This unit comprises one or two balloons, each having a shape similar, but not identical, to a half moon. These balloons, or their covers, have lines, areas or patches of adhesive film or Velcro TM on the surface that allow their position to be modified and adjusted for best placement in the beginning and later as many times as necessary. These balloons are held in place by use of a support system that consists of straps, wraps, or special shorts that allow the pressure to be built up and kept in the groin area for prevention of bleeding.

The use of two balloons, as well as special shapes of the support systems, gives a great advantage over my previous models by allowing a patient to bend his or her leg easily and to sit in a chair, which is going to occur most of the time during transportation by car, etc. The unit may also have another balloon to go over these two balloons and make delivery of a greater pressure in the area possible when the patient lays on the bed. This unit will provide the protection to the area after cardiac catheterization and related procedures, and I believe will give a great deal of peace of mind to the patients and will make their anxiety disappear. A newer means for finding bleeding after catheterization in the area is also mentioned, involving use of an electric system connected to an alarm system.

Further detail of the invention, and other features, will be seen as the description proceeds.

BRIEF DESCRIPTION OF THE DRAWINGS

FIG. 5 is a front view showing the general application of the balloon and cover to the person's body, including an alarm associated with the balloon.

FIG. 6 is a front view of the alarm of FIG. 5 showing more detail.

FIG. 6A is a fragmentary front view of a portion of the alarm of FIG. 6 showing better detail.

DESCRIPTION OF THE PREFERRED EMBODIMENT

Figure 1:
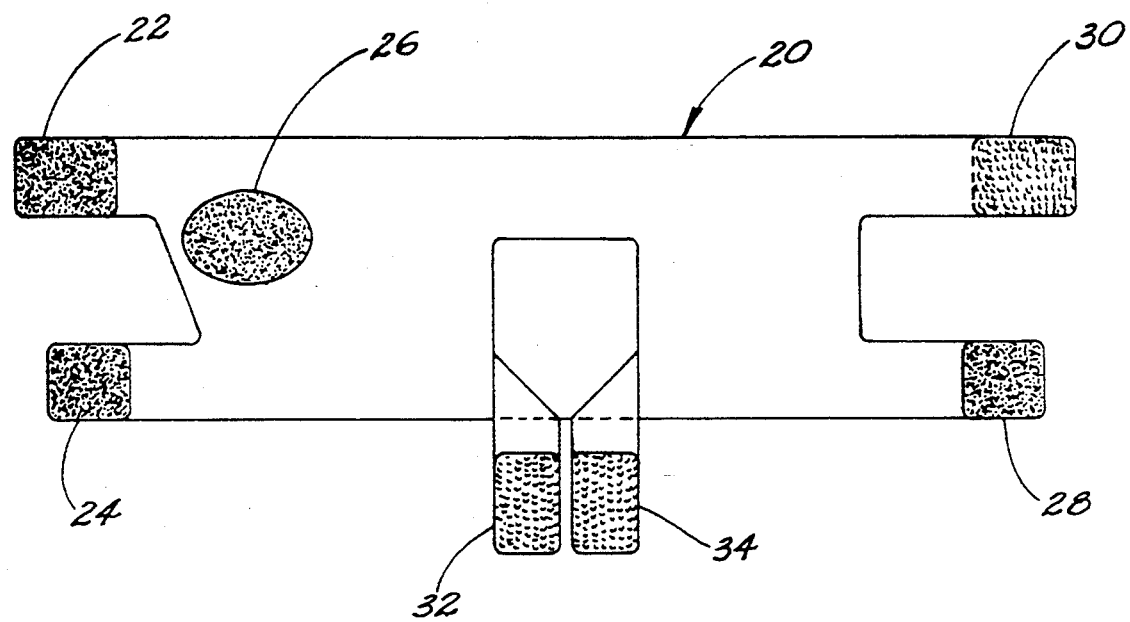
FIG. 1 is a front view of a wrap.
Figure 2:
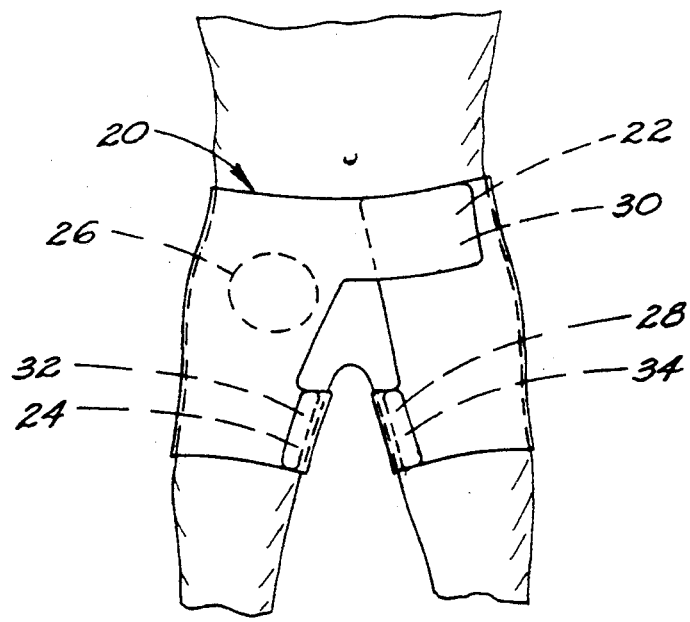
FIG. 2 is a front view showing the wrap in use on a person.

FIG. 1 shows the front view of a wrap 20 and its general appearance when opened and spread on a table. It has several areas containing Velcro TM. The soft parts 22, 24, 26, 28 of the Velcro TM are shown with straight lines, while the rough parts 30, 32, 34 are shown with dots. Parts 22, 24 are on the front face of wrap 20 as it appears in FIG. 1, and parts 30, 28 on the back face so that when wrap 20 is worn as shown in FIG. 2, the end containing soft part 22 will match and stick to part 30 to tighten the upper portion of the wrap around the lower abdomen, very much like a girdle or a belt. Part 24 will match with part 32 to wrap around the right upper thigh. Part 28 will match with part 34 to wrap around the left upper thigh. These will altogether hold the wrap tight in place.

Part 26 shown in FIG. 1 is a soft Velcro TM part and is disposed so that the back of a cover of a balloon, to be described next, will be in contact with, and stick to, it.

The purpose of this part 26 is to allow adjustment of the position of the balloon and cover to the wrap in order to fit different patients. FIG. 2 gives a general idea of how wrap 20 will look when it is worn and in place on a patient's body.

Figure 3:
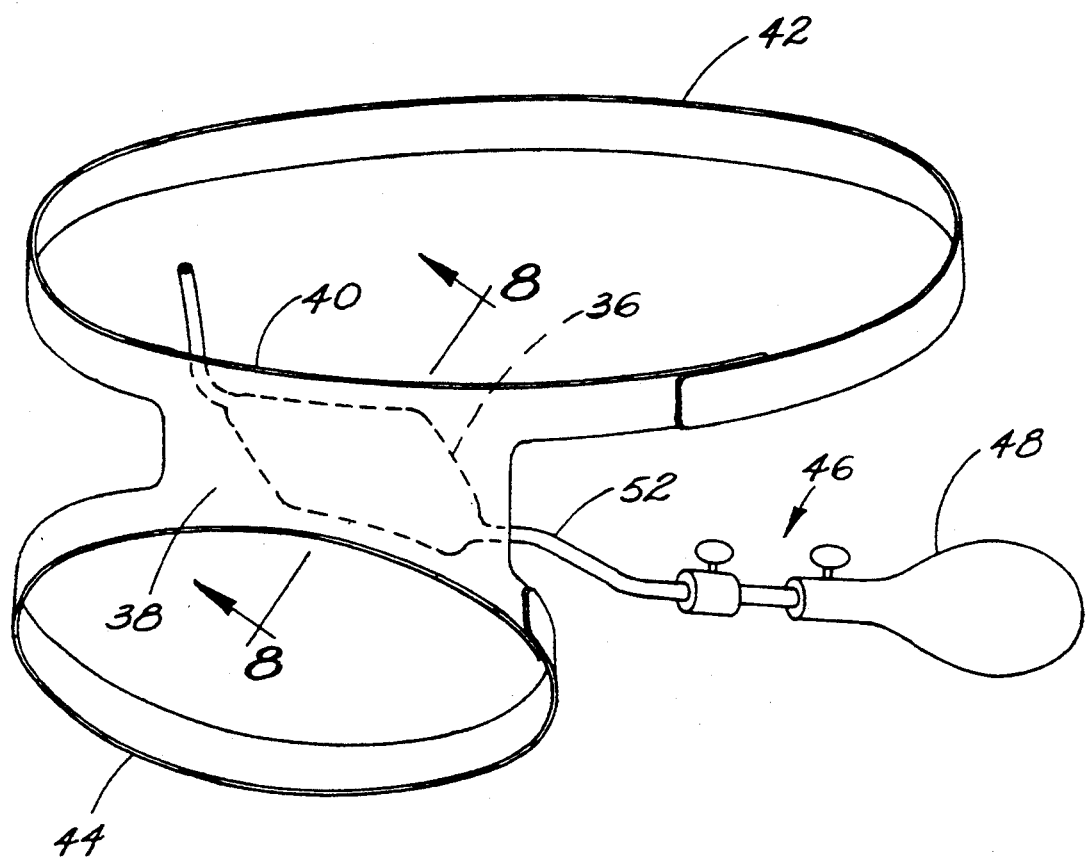
FIG. 3 is a front view of a balloon and cover.
Figure 4:
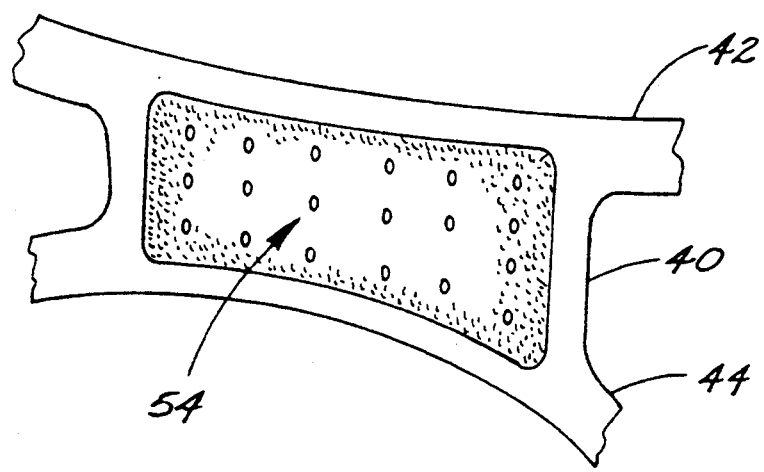
FIG. 4 is a fragmentary front view of the cover of FIG. 3 showing further detail.

FIG. 3 shows a balloon 36 inside a fabric pocket 38 of a cover 40 having straps 42, 44 extending from its corners and designed to wrap around the lower abdomen and the right thigh,. The broken area in the upper strap 42 that goes around the abdomen is intended to show the disrupted piece. The lower strap 44 is to fit the upper part of the right thigh. The general appearance of balloon 36 is shown, along with its connection 46 to an inflating part 48 as well as a tube 50 to be connected to an alarm, to be described later.

Tube 50 is at one lengthwise end of balloon 36, and a further tube 52, leading to connection 46, is at the opposite lengthwise end. The two tubes 50, 52 protrude from pocket 38.

Figure 8:
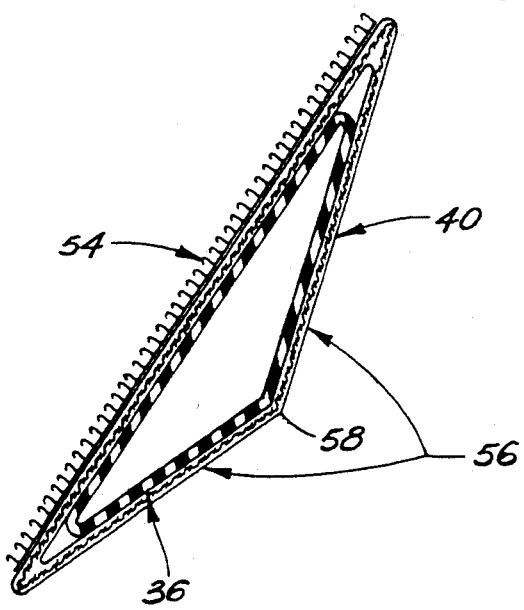
FIG. 8 is a traverse cross-sectional view in the direction of arrows 8—8 in FIG. 3.

In order to best fit and adapt to the shape and anatomy of the groin area and to mainly cover the area most liable for bleeding and hematoma, balloon 36 has an almost rhomboid shape, although it may have a different shape such as a circular or sausage-type shape, such different shapes not being shown in a drawing. As seen in FIGS. 3 and 5, balloon 36 tapers toward each lengthwise end so that it is noticeably wider in the middle than at its ends. As seen in FIG. 8, balloon 36 has a flat face 54 toward wrap 20, and an opposite angled face 56 toward the groin. Face 56 has a vertex that is to be situated in the groove of the groin line and that divides face 56 into an abdomen-confronting face portion and a thigh-confronting face portion.

Cover 40 is preferably a soft non-stretchable material to resist stretching. The cover of a regular blood pressure cuff is representative of such materials. Cover 40 has two faces: one to face the area of the groin, and the other containing a rough part 54 of Velcro TM to coincide and fit the matching part 26 on wrap 20 to hold the cover and balloon in place. Cover 40 can also be attached to wrap 20 by way of a couple of snaps. The balloon and its cover can be made from transparent plastic to allow observation of possible bleeding.

Wrap 20 is made from a durable, strong, but rather soft, fabric (similar to the synthetic fabric of many handbags and soft suitcases) designed to wrap around the lower abdomen and waist area with extensions to wrap around the upper parts of the thighs. This wrapping procedure can be achieved with the use of Velcro TM shown here and/or snaps and belt-like systems or the application of shoe tie types of techniques. The idea is to hold wrap 20 rather tightly in place to stand against pressure. When wrap 20 is held tight, then its strong non-stretchable fabric material will allow application of the force over the vessels and the adjacent areas where it is needed. The balloon's shape adapts to the shape of the groin area, and it should be strong enough to hold pressures of up to 250–300 mm of mercury.

Figure 9:
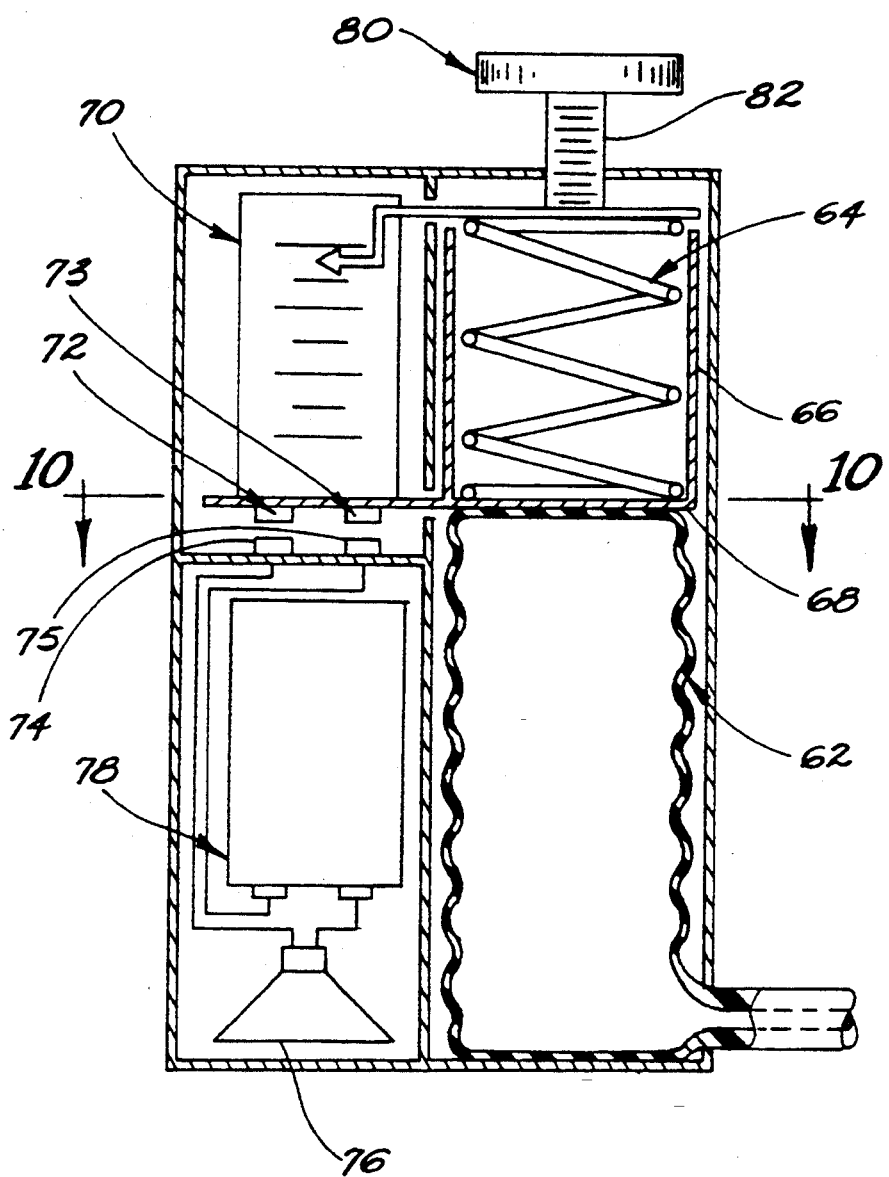
FIG. 9 is a more enlarged view of the alarm of FIG. 6.
Figure 10:
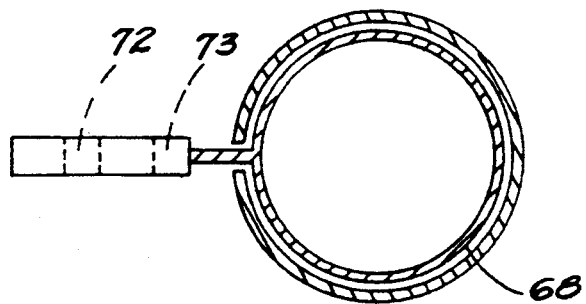
FIG. 10 is a transverse cross-sectional view in the direction of arrows 10—10 in FIG. 9.

With inflation of the balloon, the pressure will build up to be applied to the side of the vessel on the puncture side. This pressure can be monitored by connecting this part via tube 50 to the regular blood pressure monitor used in hospitals and offices or by a gauge designed for this job which is shown in FIGS. 6, 9, and 10, and which has a safety alarm part to indicate if the pressure drops. A small snap will allow the tube to be closed and the inflating device to be removed during transfers.

The alarm 60 comprises a small cylindrical box 61 having an accordion-type balloon 62 connected to balloon 36. This accordion balloon 62 will work against a circular coiled spring 64 inside box 61 and is separated by the flat, circular end plate of a cap 66 plate covering the lower end of spring 64. With a rise in the pressure inside balloon 36, this small accordion balloon 62 will be inflated, and distended and pressurized, and the pressure and distention will push cap 66 against spring 64.

Cap 66 is connected to a metal piece 68 which acts as a gauge. The gauge is to move against a scale 70 to show the relative amount of the pressure inside the balloon. If the pressure inside the balloon drops for any reason, i.e., perforation or leakage, spring 64 will push the metal piece 68 to connect its two metal terminals 72, 73 to terminals 74, 75 to complete an electric circuit and an electric buzzer 76 to sound. The circuit is powered by a battery 78. A control knob 80 comprising a screw 82 can be turned to position the top of spring 64 to adjust the level of pressure that will cause the alarm signal to sound. Turning control knob 80 also adjusts the pressure scale.

Figure 7:
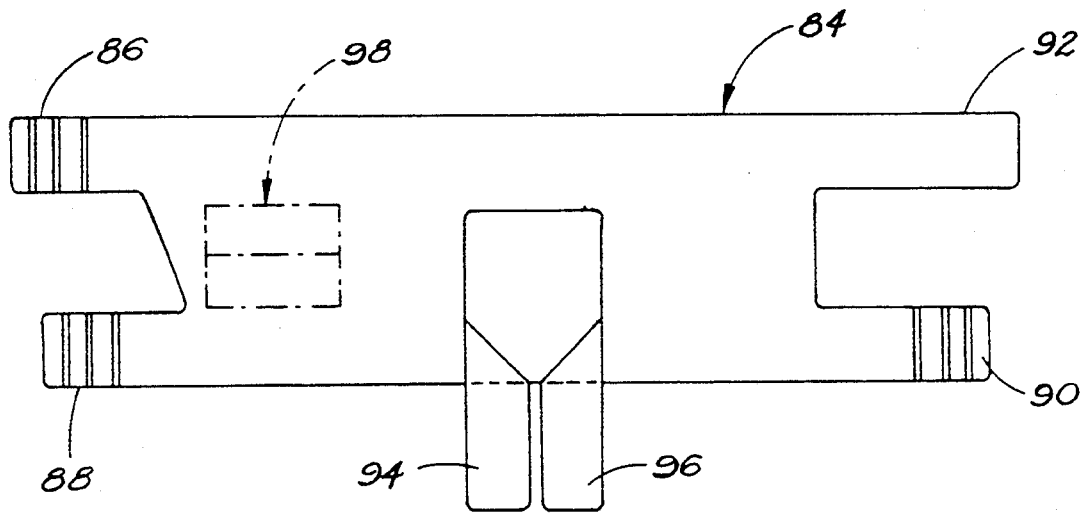
FIG. 7 is a front view of an inner wrap that may also be used.

FIG. 7 shows the front view of an inner wrap 84 and its general appearance when opened and spread on a table. It is very similar to wrap 20 mentioned earlier. It is designed to be used under the outside wrap 20 to prevent contamination of the skin and the spread of dirt and germs. Wrap 84 is a layer of thin, non-irritating, soft synthetic disposable material, with a cut very similar to the wrap 20 so as to fit inside it. In order to keep wrap 84 in place when used, it has lines of gluey or sticky areas that are covered and protected by a covering plastic or paper that will be removed to expose the gluey areas at the time of use.. The gluey areas are 86, 88, and 90.

When wrap 84 is worn, area 86 will match and stick to the back part of an area 92 after the upper part of the wrap has been wrapped around the lower abdomen. Area 88 will match and stick to an area 94 after the lower right part of the wrap has been wrapped around the right upper thigh. Area 90 will match and stick to an area 96 after the lower right part of the wrap has been wrapped around the left upper thigh.

Wrap 84 has a rectangular area 98 to register with part 26 of main wrap 20. Area 98 can be cut open and folded to the upper and lower sides (or torn) to make a window through which part 54 can touch part 26 of wrap 20 to hold balloon 36 in place. If wrap 84 is used to cover the area under the balloon, then there will be no need to have this window opened.

Wrap 84 may consist of a sheet of plastic to prevent oozing of the blood or liquids outside of the wrap. It may be designed to attach inside of the outside wrap by way of snaps, gluey surfaces, or clips, etc., before its use. The sizes, relative shapes, color, and materials of wrap 20 may vary to match different people's size and body structure as well as the amount of the pressure needed for the job to be done. The shape of the balloon and its cover may be modified to fit the anatomy of the groin area in different people with different groin anatomy, and it could be wider or have a longer diagonal along the femoral artery to cover the lower part of the abdomen for the patients whose perforation of vessels is done over and above the groin areas.

Some parts of this wrap such as the cover for the left groin and the left thigh may be eliminated when the wrap is made to be used for right groin procedures, and vice versa. Further support can be achieved for higher pressure by adding hard plastic or metal sheets to the wall of the area over the groin to enable it to stand higher pressure. The shape of these sheets may be oval or quadrilateral with mild curvature in center to match the shape of the balloon. These hard sheets may be permanent parts of the structure of the wrap or inserted inside a pocket over the groin area in the wall of the wrap when needed.

In some models, the area over the wounded vessel can be made from transparent plastics to give the chance of watching for bleeding. In such cases, the Velcro ™ part 54 will be removed from the area.

Figure 12:
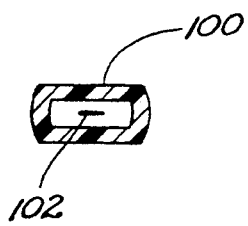
FIG. 12 is a transverse cross-sectional view in the direction of arrows 12—12 in FIG. 11.
Figure 11:
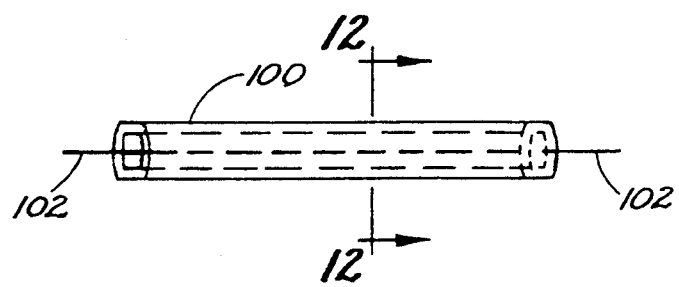
FIG. 11 is a top view of another part that may be used.

FIGS. 11 and 12 show a clear transparent plastic tube 100 with 5 by 10 mm outside size and about 2 by 5 mm inside opening and 25 to 30 cm length, designed to resist pressure and to hold a hydrophilic cotton yarn or mesh 102 inside. One end of this mesh will be positioned directly over the wound area, and the tube will extend to other end to be exposed for observation outside of the wrap. This mesh is to absorb the blood if it oozed and carry along inside the tube to allow the blood to be noted and bleeding to be observed.

When properly placed in the area after a procedure, i.e., cardiac catheterization, the balloon will be over the artery which was intervened and then, after inflation, it will put the appropriate pressure desired in the area to prevent oozing of the blood. The pressure is easily controlled and it can be checked by a gauge. A mesh inside a plastic cover to be located under the balloon may help to notice bleeding, with absorption of the blood by the mesh and discoloration of its white color when contaminated with blood.

Further support when needed can be provided with the use of a hard piece of plastic or metal located over the balloon and inside a pocket in the wrap, or in the space between the wrap and the balloon.

The balloon 36 inside cover 40 may be enough to work in some cases alone without an outer wrap 20. A soft disposable cover may be made to cover this piece in order to prevent contamination.

In summary then, the disclosed balloon 36 and its cover 40 may be said to comprise a face 56 that confronts the person's groin line and portions of the person's abdomen and thigh on either side of the groin line. The vertex 58 fits into the groin, dividing this face 56 into an abdomen-confronting portion and a thigh-confronting portion. The balloon and cover have a length extending between tubes 50 and 52, a thickness that extends in the direction of pressure application to the underlying wound, and a width that is transverse to both the length and thickness.

Figure 13:
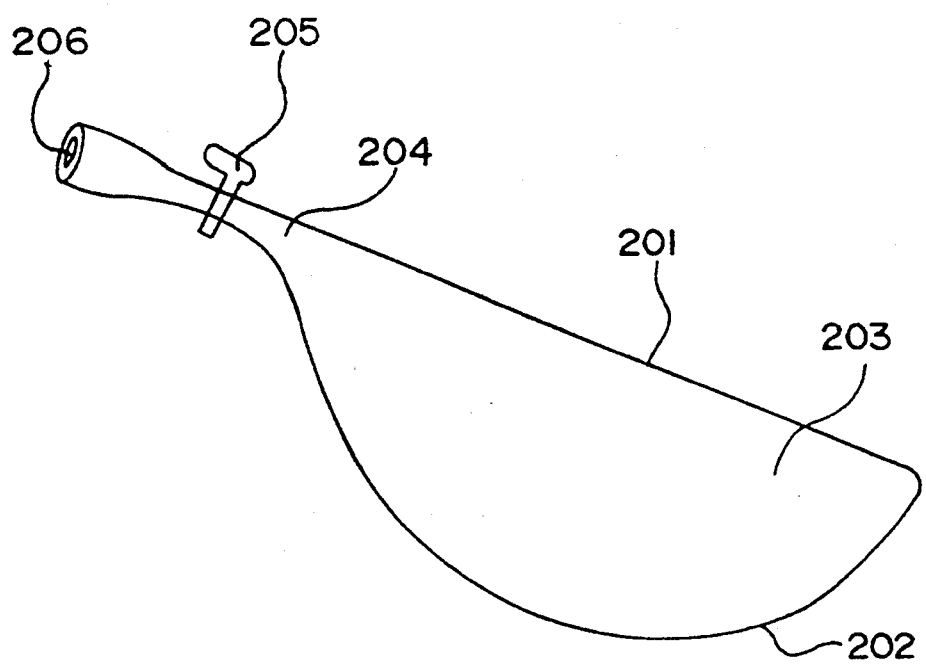
FIG. 13 is a top plan view of another balloon.

FIG. 13 shows a balloon having a straight upper rim 201 and a curved lower rim 202. The front surface is 203, and the inflation port 206 is shown with a short inflation tube 204. A valve 205 is also shown.

Figure 14:
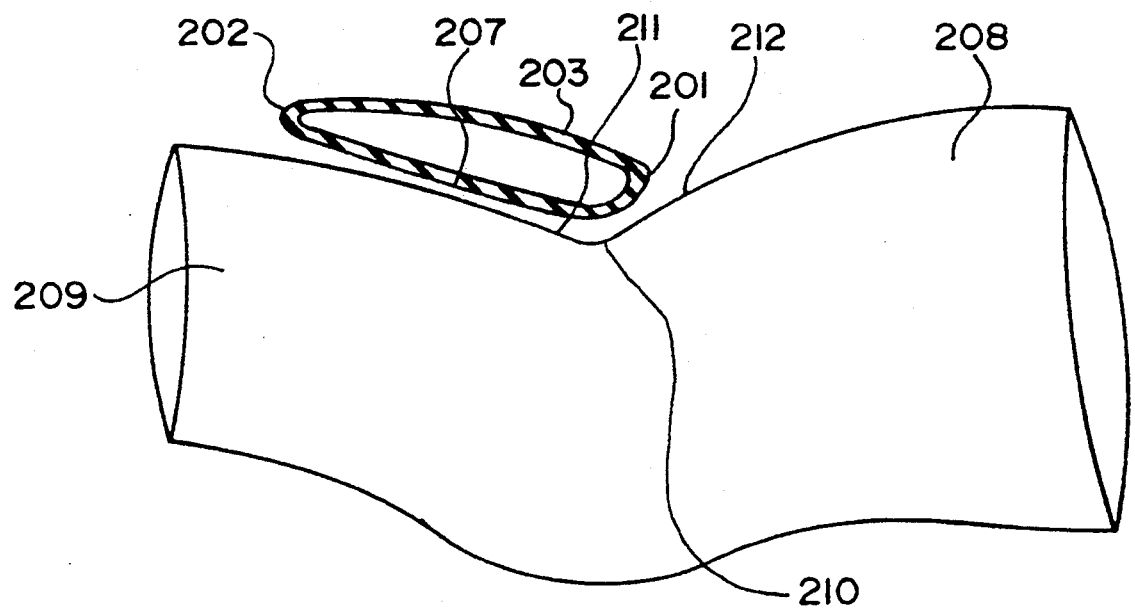
FIG. 14 is a side elevation of the balloon of FIG. 13 showing use.

FIG. 14 shows the balloon of FIG. 13 when it is placed at the site of a procedure. Here the trunk is shown by 208, the right thigh by 209, the groin line by 210, the surface of the lower abdomen near the groin line by 212, and the surface of the upper thigh near the groin line by 211. The lower surface of the balloon is shown by 207. This figure shows the general position of the balloon compared to the groin area.

Figure 15:
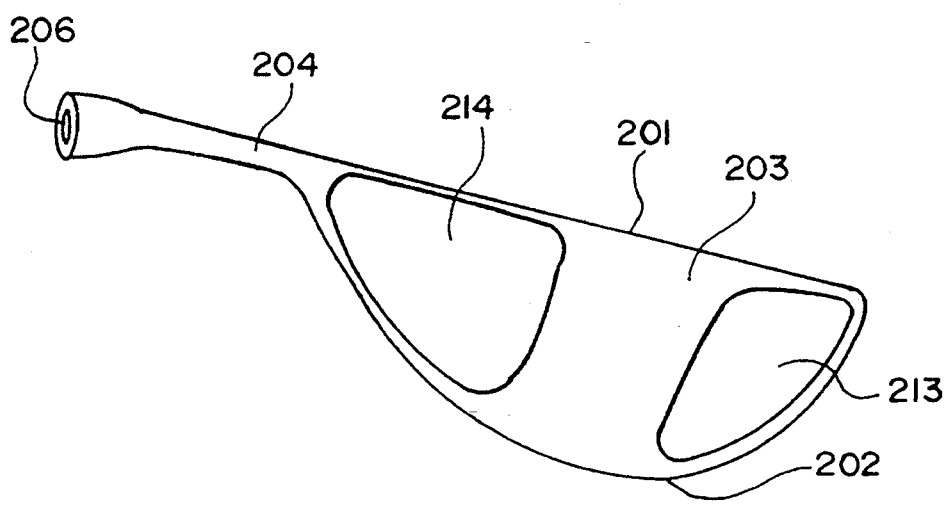
FIG. 15 shows a modification to FIG. 13.
Figure 16:
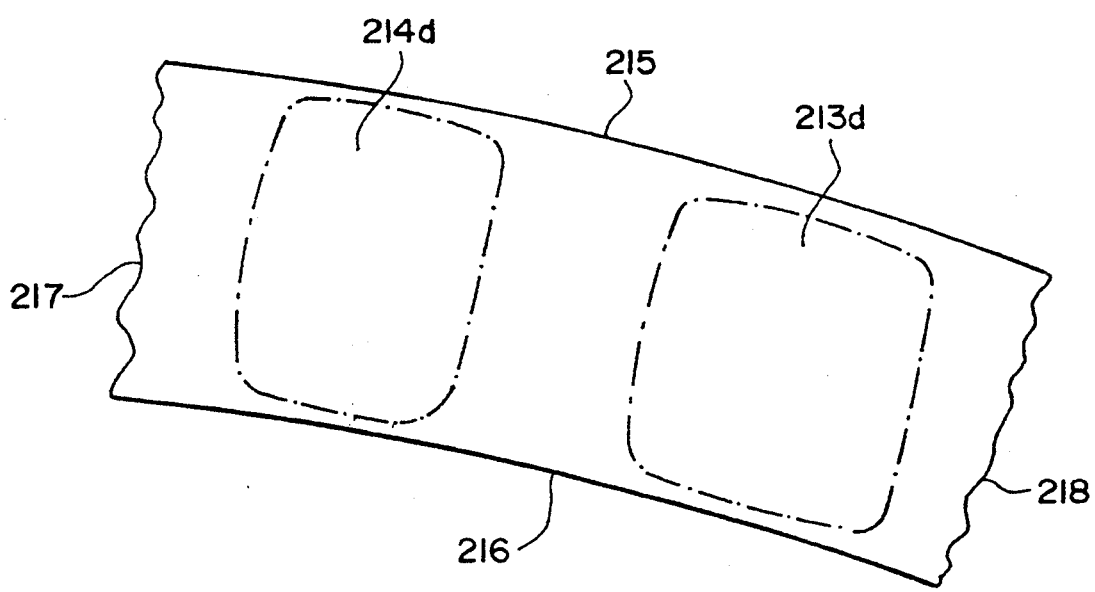
FIG. 16 shows a plan view of a portion of a support system for the balloon.

FIG. 15 shows a balloon similar to the one shown in FIG. 13, except this balloon has two patches of Velcro ™ on its top surface, here shown by 213 and 214. These are to match and be stuck to matching Velcro ™ patches of a support cover shown in FIG. 16 that stands on top of the balloon. The upper rim of this support wrap is shown by 215, its lower rim by 216, the cut of its right edge by 217, and the cut of its left edge by 218. The matching patch for patch 214 is 214a, and the matching patch for patch 213 is 213a.

Figure 17:
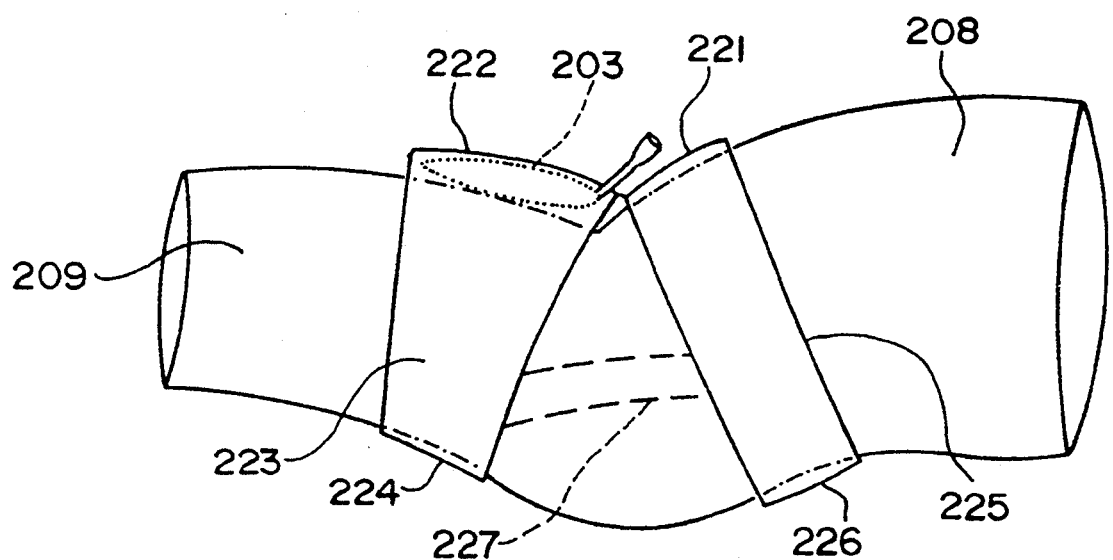
FIG. 17 is a side elevation showing use of the support system.
Figure 18:
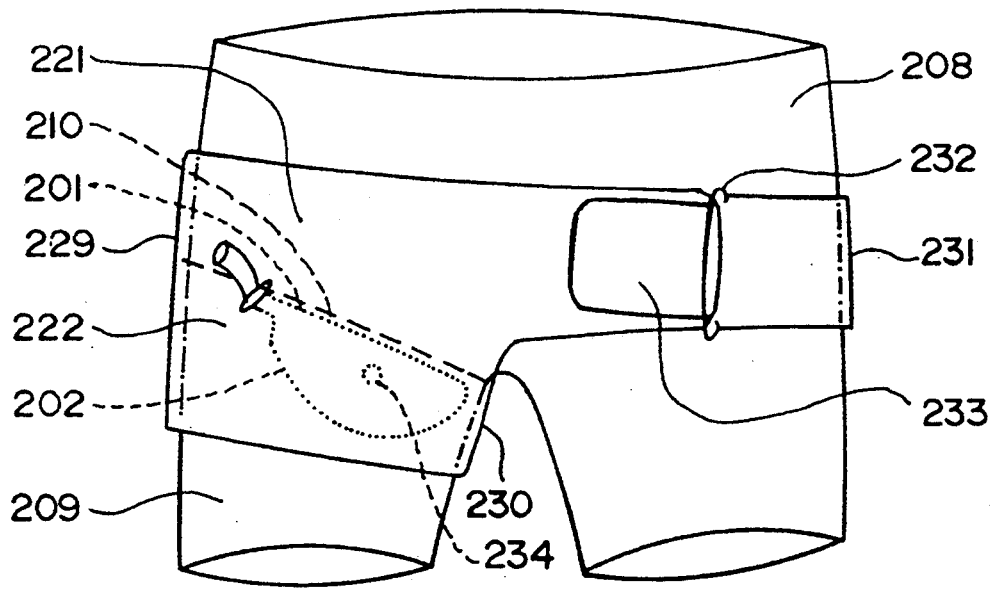
FIG. 18 is a top plan view of FIG. 17.

FIGS. 17 and 18 are to help the reviewer notice the placement of the balloon and the wraps holding it on the body. The balloon is placed on the upper surface of the right thigh, and it is held in place by a wrap that goes around the thigh as well as the waist area. The upper surface of the wrap over the balloon is shown by 222. The inner side of the wrap which is around the right thigh is 223; the part under the right thigh is 224; the part on the lower abdomen is 221; the part that is in the side of the waist is 225; and the lower part of the wrap under the waist is 226. Please notice that in this view for the purpose of presentation, the left thigh is not shown at all.

FIG. 18 shows the front view of the balloon and the wrap in place on the body. The balloon is placed on the upper surface of the right thigh, immediately under the groin line 210. The hole in the skin is shown by 234. The upper wrap goes around the waist, and 231 shows the left side of the wrap. 232 shows the snap that the end 233 of the upper wrap goes through to make a U turn and come and stick to a matching Velcro TM patch on its own rear surface. The front part of this wrap continues in the right groin area to cover the surface of the balloon and then to wrap around the upper thigh at 222, the right side of this part being shown by 229 and the inner part by 230.

Figure 19:
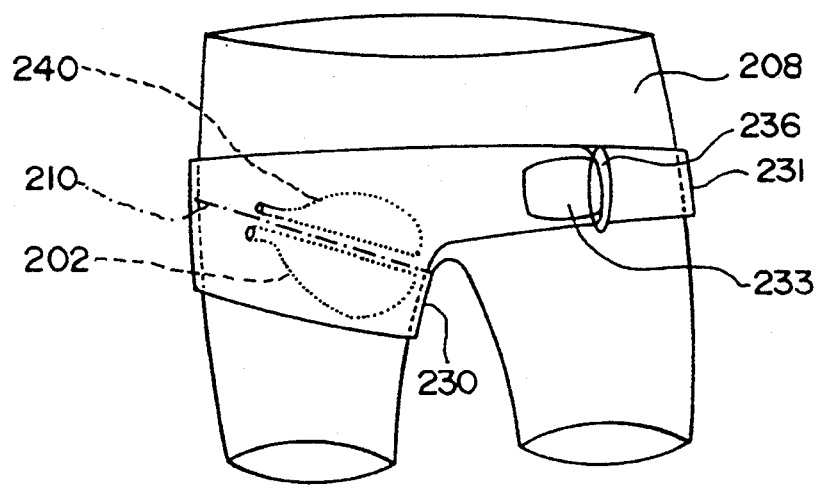
FIG. 19 is a top plan view, similar to FIG. 18, but showing a further balloon.

FIG. 19 is very similar to FIG. 18 except here the balloon is a double balloon, one shown by 240 standing on the lower abdomen, and the other being the balloon of FIG. 13 standing on the upper part of the groin. The upper wrap goes around the waist, with 231 showing the left side of the wrap. 236 shows the snap that the end 233 of the upper wrap goes through to make a U turn and come and stick to a matching Velcro TM patch on its own rear surface. The front part of this wrap continues in the right groin area to cover the surface of the balloon and the inner part of this wrap is shown by 230.

Figure 20:
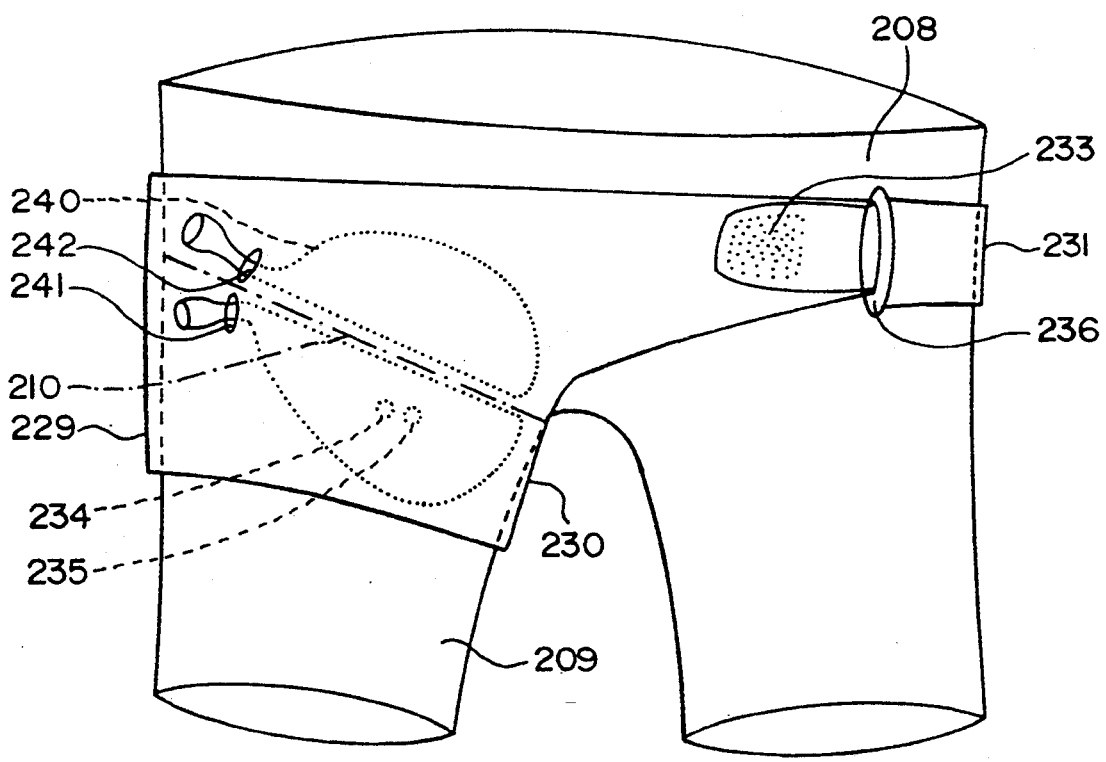
FIG. 20 is an enlargement of FIG. 19 to show more detail.

FIG. 20 is larger to show more details. The lower balloon is standing on the upper part of the groin over two holes in the skin shown by 234 and 235. The outer side of the wrap that covers the lower balloon 229, and the inner part of this wrap is shown by 230. The inflation ports of the upper and lower balloons have gone through the holes 242 and 241 respectively to come out of the wrap. These holes 242, 241 are in the wrap.

Figure 21:
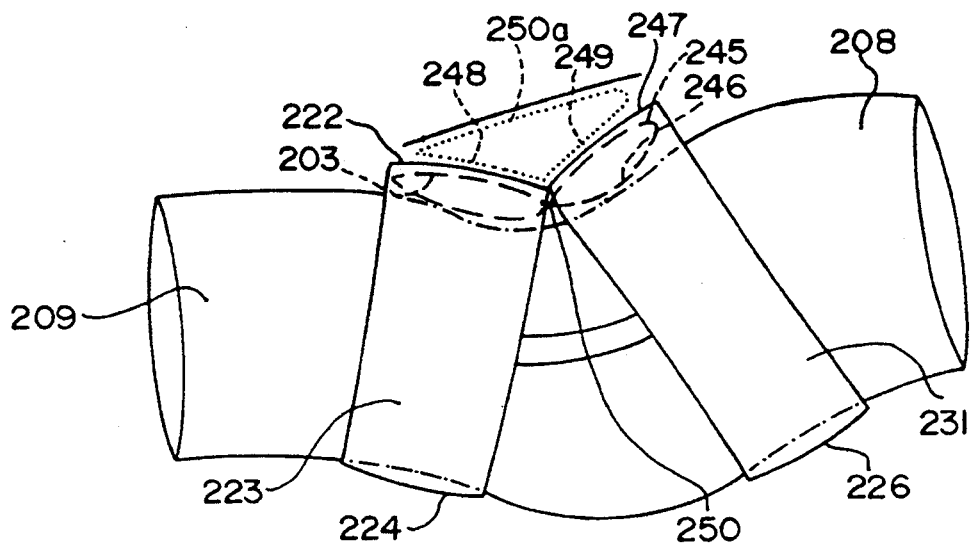
FIG. 21 is a side elevation of usage like FIGS. 19 and 20, but showing a still further balloon.

FIG. 21 shows the lower balloon connected to the upper balloon by a connection piece 250. The upper balloon is placed on the lower abdomen immediately above the lower balloon. The upper surface of this upper balloon is shown by 245 and the lower surface of it by 246. The lower balloon is held in place by the lower part of the wrap. This wrap goes around the thigh as well as the waist area. The piece of the wrap over the upper balloon is shown by 247, corresponding to 221 in FIG. 18. Left thigh is not shown. A third balloon 248, 249, 250a having a triangular shape fills the space between the upper and lower balloons so that after inflation these balloons combine to generate pressure on the groin area and act as a solid continuous unit applying pressure to the upper groin, lower abdomen and the groin line. This balloon is held in place by a support system like a wrap 251 that goes over the groin and waist wrap.

Figure 22:
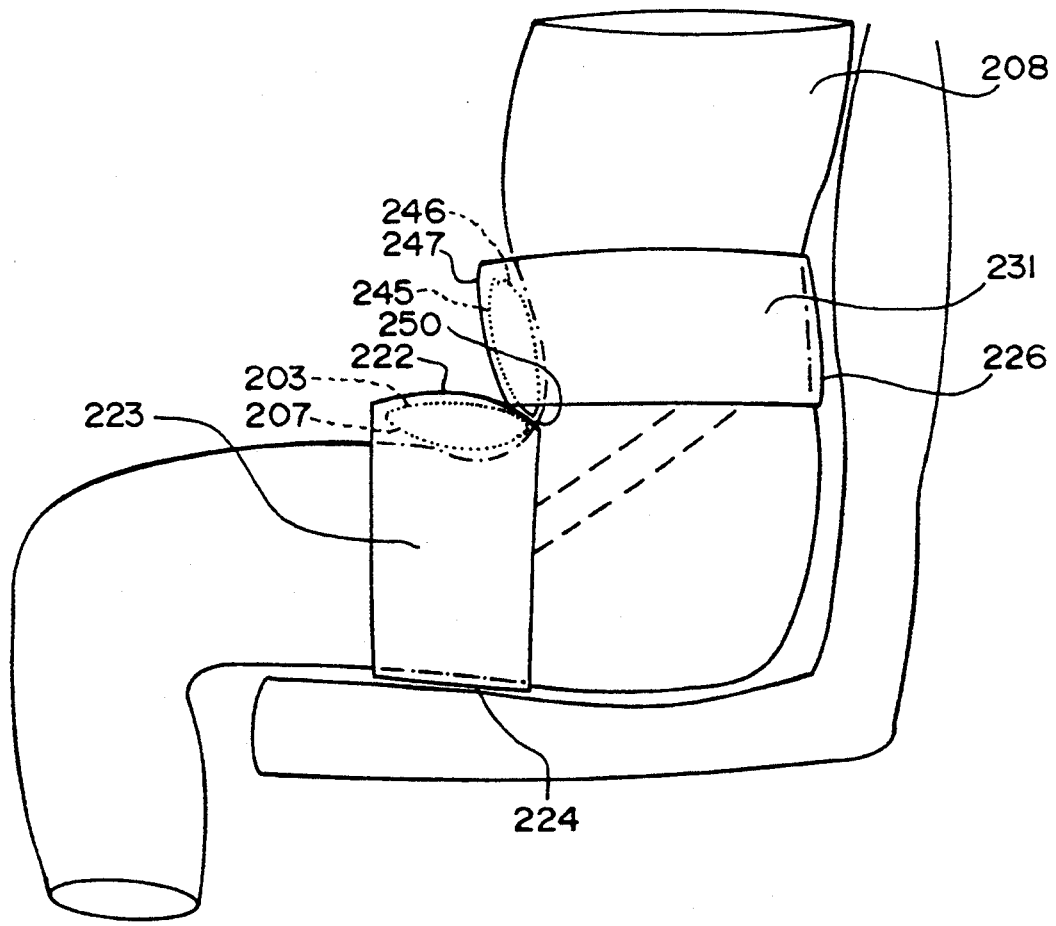
FIG. 22 is a side view showing how a patient can sit up with my invention.

For the purpose of FIG. 22, the left thigh is also not shown. FIG. 22 is to illustrate the benefit of this unit when the person is using it. Here the patient is sitting on a chair. The thigh has a 90 degree angle with the trunk. Here again double balloons are in place, held by a wrap that is not continuous and connected in the back to allow the person to sit comfortably. In this view the lower balloon is on the upper surface of the thigh; the upper balloon is on the lower surface of the abdomen; and both of them are held in place by the wrap.

Figure 23:
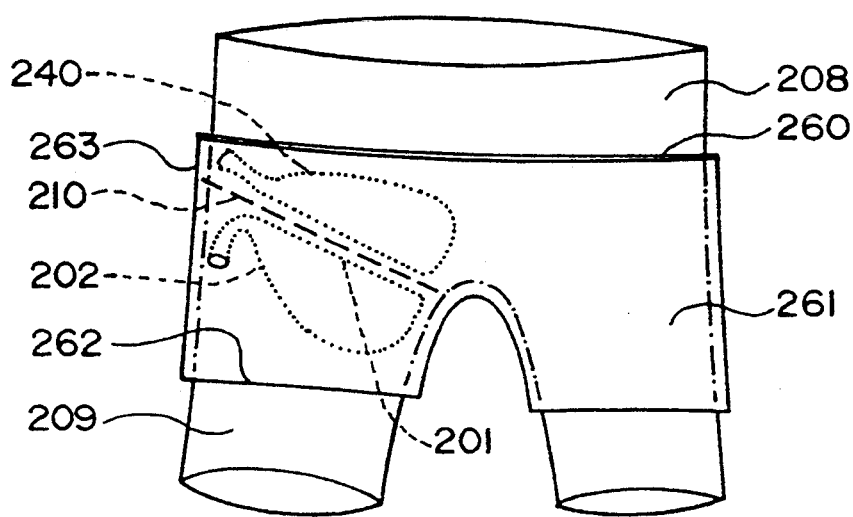
FIG. 23 is a plan view showing usage of balloons with shorts.

FIG. 23 is very similar to FIG. 19 except FIG. 23 is to give an idea about the shape and construction of shorts used to hold the balloons in groin and lower abdomen area. Here the balloons are like those of FIGS. 19–22. The upper part of the shorts is 260; the right side is 263; the right leg of the shorts is 262; and the left leg of the shorts is 261.

Figure 24:
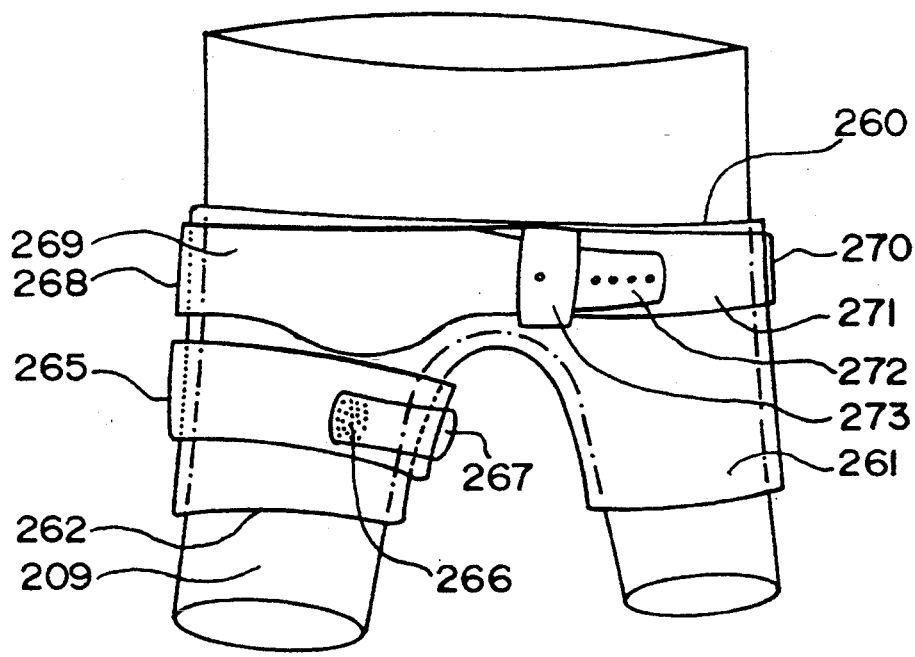
FIG. 24 is a view similar to FIG. 23 showing the addition of wraps.

FIG. 24 shows the outlook of the shorts shown in FIG. 23. In this view the patient is wearing the shorts. Here an upper strap is shown by 269; the right side of the strap by 268; the left side of the strap by 270; and the end 272 of the right side of the strap comes and goes through a snap 273 at the end of the left end 271. A lower strap 265 has an end 266 that makes a U turn on a snap 267 and comes and sticks to its own back.

Figure 25:
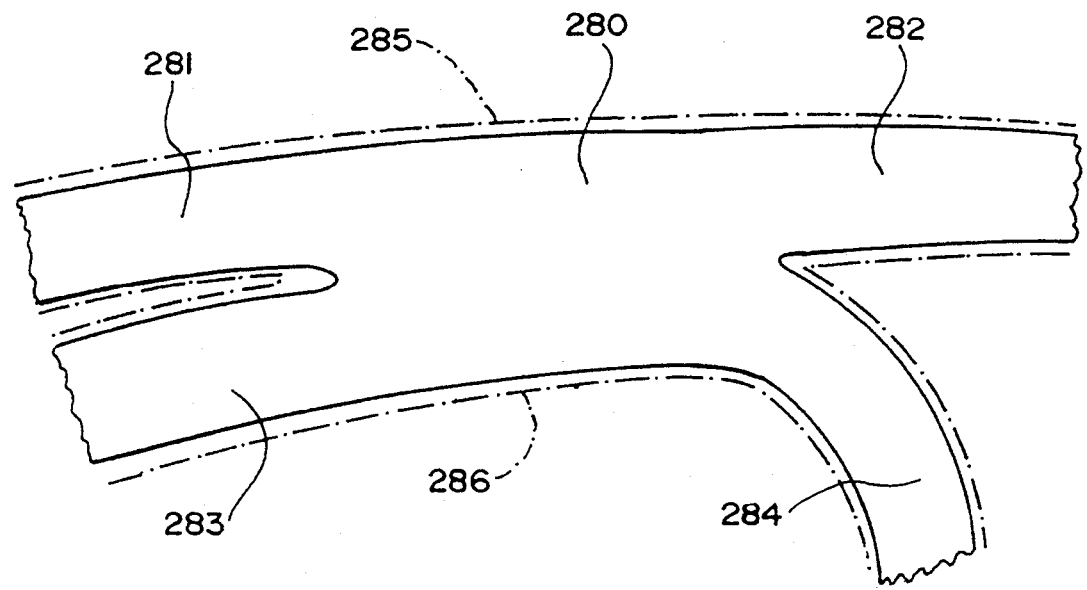
FIG. 25 is a plan view of a portion of an inner cover.

FIG. 25 shows the front outlook of an inner cover, as laid on a table. 280 shows its body which will stay on the front of the patient over the upper groin and lower abdomen. 281 and 282 are pieces that will stay under the upper wrap or strap (the total length is not shown), and 283 and 284 will stand under the lower wrap or strap. This figure shows a rim 285 as well as a rim 86; their border is shown by a dot and dash line. This rim is to overlap the edge of the support cover and is to be turned to stick to the back of the rim of the support system to prevent the edge of the support system from irritating the skin of the patient. The surface of this unit may have bands or patches of adhesive or Velcro TM.

Figure 26:
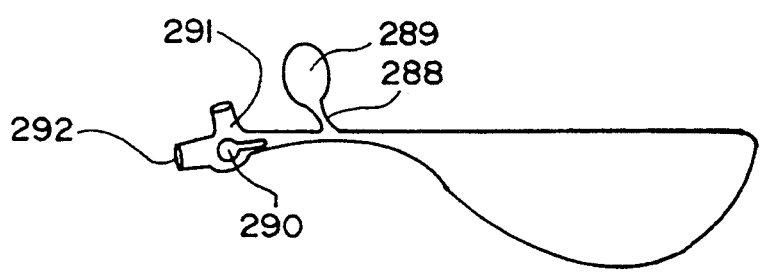
FIG. 26 is a plan view of a balloon with a pressure indicator.

FIG. 26 shows the general look of a balloon similar to the one shown in FIG. 13. FIG. 26 is primarily to show a small balloon 289 that is connected to the inflation tube for the purpose of showing the pressure inside the larger balloon. Balloon 289 has a connecting tube 288 as shown. The main balloon ends with a three way stopcock having an end 292, a side opening 291, and a control arm 290.

Figure 27:
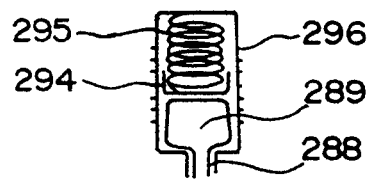
FIG. 27 is a cross sectional view through the pressure indicator on a larger scale.

FIG. 27 shows a unit which provides some measurement of the pressure inside the balloon. This unit is made from a clear plastic cylinder 296 that has the small balloon 289 inside. This balloon 289 is standing against the flat cover 294 of a spring 295 so that when the pressure of the air inside the balloon 289 is increased the flat cover of the spring moves and squeezes the spring. Its movement can be seen through the clear plastic wall of the cylinder to give an approximate idea about the inside pressure. The side of the clear plastic will be marked and standardization may be made against a mercury sphygmometer, which will give a rough idea.

Figure 28:
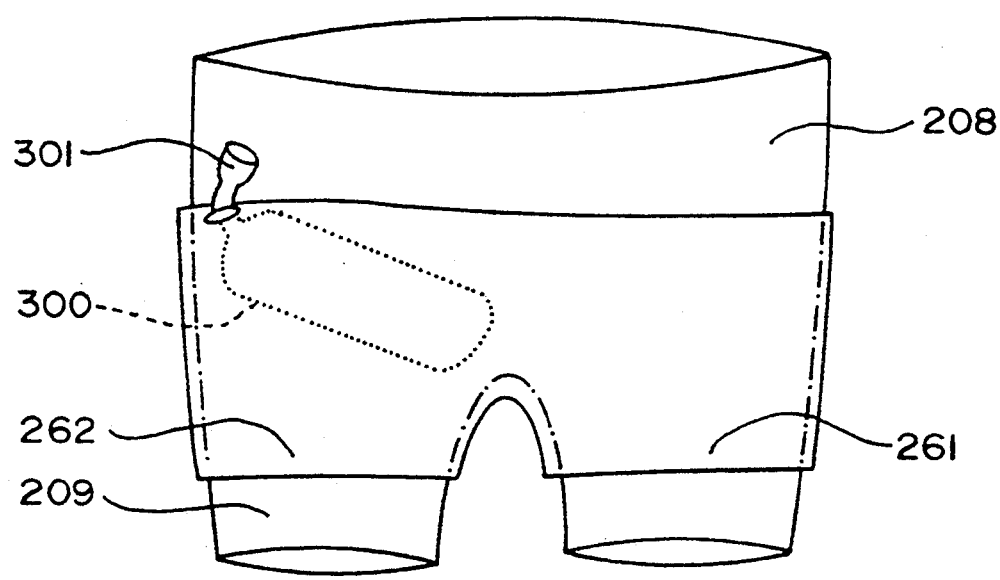
FIG. 28 is a plan view of an embodiment for treatment of hernia.

FIG. 28 is very similar to FIG. 23 except this view is to give an idea about the shape and construction of a shorts that is to be used on patients with inguinal hernia. Here the balloon has a shape more like a rectangle, and it also has the curve to match the area (not shown here) and is to stand on the hernia area. The balloon 300 is shown with dotted line, and its inflation port by 301.

Figure 29:
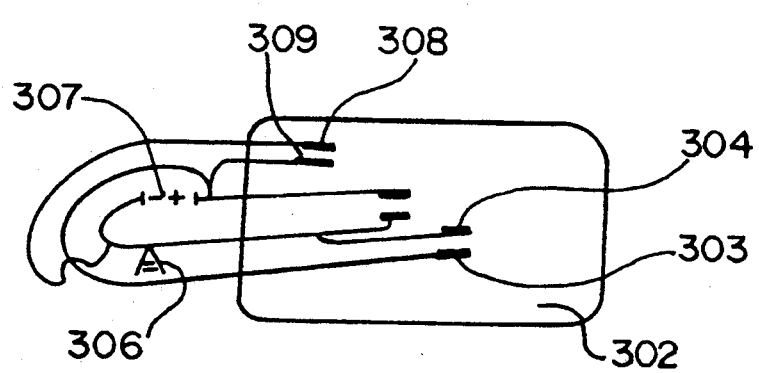
FIG. 29 is a schematic diagram of an electric system and alarm for detecting wound bleeding.

FIG. 29 illustrates the unit which is for sensing contamination by blood. In this view the body of a cover is shown by 302. Electrodes 303 and 304 are connected to a battery 307 and an alarm 306. Here three pairs of electrodes are shown, one in the middle which is not marked, and another pair 308, 309 which is standing further than the other ones. The idea is to have different levels of these sensor leads that one of them may be activated to indicate bleeding. The switch for turning them off is not shown here.

Figure 30:
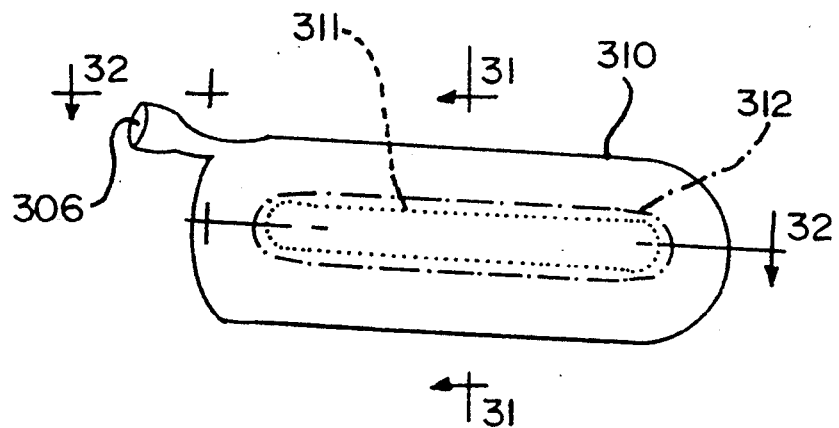
FIG. 30 is a plan view of another form of balloon.

FIG. 30 is a balloon that is to be used after hernia surgery (it can also be used in other surgeries) and during the period that the site of incision is still sensitive. This is a unit that has a shape to match the area of the hernia. The dotted line in the center 311 is to show the area to be protected from the pressure of the balloon by a rigid or semi-rigid plastic shown by 312. Here the inflation port 306 is shown, as well as the border of the balloon by 310. This figure gives a general idea about the shape of the balloon although it may have different shapes and sizes.

Figure 31:
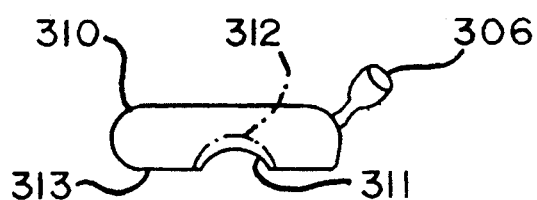
FIG. 31 is a transverse cross section through the balloon of FIG. 30 along line 31—31 in FIG. 30.
Figure 32:
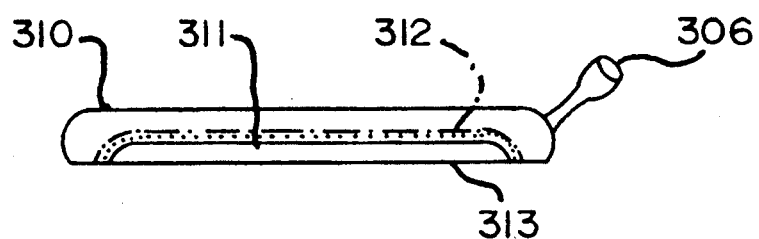
FIG. 32 is a longitudinal cross section through the balloon of FIG. 30 along line 32—32 in FIG. 30.

FIGS. 31 and 32 show the lower surface 313 of the balloon, the curved protective area 311, the outer surface of the rigid or semi-rigid protective plastic piece 312, and the border 310.

DETAILED EXPLANATION OF THE INVENTION

Reference is made to my pending applications Ser. No. 07/800,085, now U.S. Pat. No. 5,263,966 and Ser. No. 07/967,379, especially FIGS. 22, 23, 24, 25, 26, 15, and 16, and pages 33–34 about units for herniorrhaphy and pages 37–38 under the title, "Use of this unit after Coronary Angioplasty", in the latter.

As mentioned earlier, both physicians and patients are deeply concerned about complications at the site of intervention in the groin after cardiac catheterization and related procedures such as angioplasty. I believe the need for protection and peace of mind is real. This concern is such that usually there are some statistics about the complications of cardiac catheterization in each cardiac center, and the lower it is, the better is sounds for the institution. But to the best of my knowledge there is no unit available for protection of the groin that a patient can take home, except my own previous invention under the above patent applications, which is now being modified and improved in this application.

Basically this invention is a unit that, like my previous inventions, uses a specially shaped pressurized balloon to prevent bleeding in the groin area after cardiac catheterization and related interventions. This pressurized balloon is designed to be held in place by use of special straps, wraps, or shorts. However I have reached to conclusion that in some cases, use of the previously mentioned single balloon would not be as effective. During transportation and times that a patient has to sit on a chair, a single balloon going from lower abdomen to upper groin may cause problems such as disfiguration and possible dislocation of the balloon and wrap and potential malfunction. This is due to the fact that the pressurized balloon may not bend easily in the groin area when it is held in place by a wrap. Again this may cause dislocation of the balloon which may cause the balloon to be less effective and not to serve the important intended purpose. So in my mind this cannot be used in patients who are going to sit on a chair during and after discharge. Therefore in order to provide a patient with a functional unit that can be used outside of the hospital or clinic, an improved version of my previous model is presented here. This modification and improvement contemplates the use of one, two or more balloons with special shapes that allow the patient to assume sitting position without much discomfort. The modification also applies to the support system as well that will have a shape that allows patients to sit without much disfiguration and lack of function of the unit.

Also during many years of my practice I have noticed the great concern of patients with hernias about their problem and their worries about whether their hernia may enlarge, deteriorate, etc., with different motion. I have noticed that this concern and anxiety are real, and there is a big difference in mentality of different people, and their situations. The surgery for hernia, although very useful and beneficial, and most of the time simple, cannot be done all the time since the timing for all patients may not be feasible due to concerns such as acute major sickness like heart attacks, terminal cancer, or severe lung disease, etc. These may not allow a patient to have surgery as a person may wish, and so a temporary alternative will be very useful many times. Also after some surgery when the constructed tissues are still weak, use of support can be very useful and beneficial. For these reasons I believe with minor modification of this unit a unit can be made to support the area of the hernia in many cases.

For this purpose a unit can be made with a longer balloon (300, FIG. 28) to be held over the inguinal hernia area and operated site by a support system after the surgery. In such cases the pressurized balloon is held by a wrap to prevent the hernia from bulging and the site of operation to be pressured by the intra-abdominal pressure.

As I have specified in my previous application, (pressure bandages and dressings), the center of this balloon may be made to have a free space along the line of incision shown by dotted line 311 to prevent pressure to the incision site when it is tender and sore. This area can be protected by a piece of rigid or semi-rigid plastic shown by dot and dash line of 312. The fact that the balloon itself, its location, and the pressure inside the balloon can be changed easily gives freedom and many choices for this unit. This can be very helpful in different circumstances when there is a need for support and pressure changes. For example, we can imagine the case of a patient with hernia who develops a case of severe cough due to bronchitis, as many people do. During the episodes of severe cough, there is a greater need for support than in a relaxed normal condition. Or if a person with hernia is to move heavy objects manually, that will automatically increase the pressure inside the abdomen. Again, the need for support increases and therefore my invention turns out to be very useful by giving adjustability and options. This technique with minor alternations may be also used and be beneficial in the other cases of abdominal hernias for physical and psychological support.

Special shorts can also be made to have a pocket to hold the balloon and to be kept tight by one or two straps.. That will allow the patients to use them easily and practically whenever they wish and not to worry about their hernia popping such as in some of my patients. I believe that use of this unit will bring significant peace of mind to these patients as well as providing significant (although temporary) protection.

The Balloons and Their Shape:

This unit is made from one (FIGS. 13 and 14) or two balloons (FIGS. 19–22), each having a shape similar, but not identical to, a half moon. The balloons or their cover may be connected to each other by a band or fabric along their straight line edge. They may also be used as two separate and independent balloons. In some cases use of one lower balloon may be sufficient (FIGS. 13 and 14), that in that case, the balloon has a line 201 that matches the direction and shape of the groin line 210 and is held close to it. The exact placement of this balloon will be related to the case and the judgment of the physician. This balloon has a lower rim or edge 302 that is somewhat similar to the curve of edge of the half moon, although the inner half side of this balloon is wider with more surface than the outer side. This is to cover the length of the vessels under this area. From the other side, the thickness of the balloon close to the groin line (close to 210 in FIG. 14) will be much thicker to fill the deeper space which exists in the groin line area. This shape by itself is important and I believe gives a great advantage to this balloon to function much effectively. The upper balloon (240, FIG. 19) is very similar to the mirror image of the lower balloon. With some differences that can be noted in FIGS. 19 and 20, the lower balloon is placed on the area where the intervention has taken place and needs to be pressed. The upper balloon is placed on the lower abdomen over the main vessels going to the thigh area. These balloons will have an inflation port that will allow the air to be inflated, and one rubber hose (not shown in figures) may also be connected to the balloon to allow connection to a pressure monitor of one kind or another to allow monitoring the pressure. Importantly in some cases, fluids such as iced water may also be injected, or pumped, into these balloons. For this case, the balloon will be made from appropriate material to tolerate the cold temperature for such use. Some air may still be left inside the balloon for application of pressure. The use of iced or cold water is to help to prevent more oozing of the blood in some cases. A person may wish to use warm water later. A three way stopcock or a valve (205, FIG. 13 and 290, FIG. 26) are used to prevent air or fluid leakage. The three way stopcock may be connected to the very tip of the inflation port to allow the control. A one way valve (not shown in picture) may be used instead in the tip of the inflation port of the unit so that it will allow injection or suction of air or fluid into, the system to occur but not to allow the air to move in and out after the inflation syringe or balloon is disconnected.

These balloons may have a patch of Velcro TM or adhesive film on some part of their surface to allow the balloon to be stuck to the matching pieces of Velcro TM from the support system so that the position of the balloon can be adjusted relative to a patient and the support system, considering the anatomy of the area as well as the site of intervention, etc. This design will be helpful since there is significant variability between the size of the people and shape of their groin area due to height, weight, truncal obesity, etc. For this reason there will be different sizes and shapes of these balloons to allow one particular one to be chosen for a given patient.

When two units are used, one balloon will stay in the upper part of the groin and the other one in the lower part of the abdomen. The inside of these balloons may be connected to each other so that they could be inflated by one inflation port or most commonly they will have two different openings for inflation so that different pressure build up can occur in their cavities. The balloons may be connected to each other along their straight edges by way of straps or bands or continuation of their surface material. Alternatively a piece of wide adhesive tape can be used to tape these two balloons to each other, after their position is chosen. In the cases where the balloons are connected (FIGS. 21 and 22), the connection line 250 will be thin to allow the bending to occur along that line when patient assumes a sitting position.

The use of two balloons will allow the patient to bend his or her leg while sitting in the chair, and the space between the balloons lets such function to occur while the pressure is still being applied to the areas under the balloons on upper and lower sides of the groin line. Sitting position will be assumed most of the time during transportation by wheelchair, car, etc., and this is the time that this unit shows its significant advantage over my previous invention. Also in order to apply enough pressure when patient is in supine position a third balloon 248, 249, 250a, FIG. 21, may be used that will go over those two balloons like a wedge and stay in the area between them so that the balloon can expand and fill the space and gap between the upper and lower balloons to deliver extra pressure needed for better function when patient is in supine position. This will be an optional use.

The Choice of Balloons:

The fact that this application mentions three balloons will bring the question of when these are needed to be used and if they are the same. For this reason I explain the following:

1. The single balloon is to be used when the patient had simple cardiac catheterization and the area looks very much clean without much hematoma or complication.

2. Double balloons are recommended when there has been significant work done in groin with possible hematoma and extravasation of the blood during cardiac catheterization. This unit is recommended in all cases of transcutaneous angioplasty in which the size of the sheaths are larger and the intervention is usually much more intensive.

3. The third balloon is to be used when a patient is in supine position and when extra pressure seems to be necessary.

The Support System:

In order to hold these balloons in place and to apply pressure, different techniques are chosen as follows:

A. Use of Straps: The balloon may be made with a cover that has a tight non-stretchable cover in its rear side (that is to stay away from patient). This is to allow the application of pressure in the area. A softer more stretchable cover in the front (that is to stand against the wound area and this construction will allow the transmission of the pressure to the wound area). The outer cover of the balloon also has an extension like a flap that is to stand on the lower surface of the abdomen and to be held in that area securely and tight by connection or the overlap of a strap or wrap that goes around the waist. The side ends of the balloon cover are connected to a pair of straps that go around the groin to be held tightly in place. The straps are connected to each other by snap or Velcro TM patches. These straps are soft and non-stretchable, similar to the material used in cars' seat belts. These straps will hold the balloons in place securely and comfortably.

B. Use of Wraps: The balloon may be kept in place with use of wraps (FIGS. 17-20) that go over the balloon/s and to give the chance of building pressure against it. This wrap will go around the groin (229, 230, FIG. 18) and the waist (221, 225, 226, FIG. 17) and (221, 231, FIG. 18) to be held in place tight. Their ends to come together to be held in place by snaps or Velcro ™ patches (232,233, FIG. 18). Here again in order to have: the unit study as well as comfortable and ideally functional the wrap has a shape that is connected in front, but separate in the back (FIGS. 17–22) so that very importantly the waist part is allowed to separate from the groin part when patient is sitting on the chair. The upper part of the wrap (247, 231, 226, FIGS. 21, 22) goes on the waist area and the lower part (222, 223, 224, FIGS. 21, 22) goes around the upper part of the groin to hold the unit in place securely and comfortably.

C. Use of Special Shorts: A special shorts (FIGS. 23, 24) may also be made to hold the balloon in place and be supported by straps. This will be very practical and easy to use in some patients. This shorts will be made from cotton or similar material used in making regular shorts, except it will be slightly tighter and have a pocket in the right or left groin area (wherever the procedure is done, most commonly the right side) where the balloon is supposed to stand. This pocket has a size and shape to accept and hold the balloon inside it. This pocket (not shown) has a means for holding the balloon inside itself securely by way of a zipper or a flap with buttons, etc. There can be means for adjusting the size of the pocket by way of having different buttons or holes in the flap and side, or similar way, or use of Velcro ™ patches, so that to some degree the position of the balloon could be changed. A strap (268–271, FIG. 24) is connected to the outside of the shorts to allow it to go around the waist like a belt and to be tightened in place by a belt-like system (272, 273, FIG. 24) that looks like a belt. Also another nicely made strap goes around the thigh area (265, FIG. 24) over the shorts and balloon and is tightened by Velcro ™ patches (266, 267, FIG. 24). A fake strap may also be made in the left side to make a design so that people will not look at it as a therapeutic device and so that patient may walk with it in warm weather. This combination may not only be easy to use, but easy to accept and tolerated by some patients. The balloon may be incorporated in the wall of the shorts in the factory before delivery to the hospital. The shorts may also have a design for use with two balloons (FIG. 23) which would need the incorporation of pockets for two balloons: one higher pocket in the lower abdomen area; one lower in the upper groin area; and both of them to be supported by straps as mentioned. In order to control the position of the balloon relative to the straps and wound in models where the balloon is tightly placed inside the pocket of the shorts, the outside of the pocket has a patch of Velcro ™. The inner surface of the straps has the matching piece of Velcro ™ so that the attachment of the strap on the pocket when the balloon is appropriately placed holds the balloon securely in place as desired.

These shorts may also have a layer of thin plastic inside to prevent leakage of blood or fluids in and out of the wound place. These shorts will be made in different sizes, shapes, and colors to allow selection and matching of the best one for a given patient. These shorts may have an opening in the front to allow urination without removal, and they may also have a flap in the back that can be opened to allow defecation to happen in certain circumstances where patient is not able or should not take the unit off and put it back easily. In such cases after the patient had a bowel movement, a small pad is placed on the anal area to prevent contamination of the shorts until more appropriate cleaning will be available for the patient. Obviously, this is for unusual circumstances that may occur for a certain patient, but it can be very useful in that circumstance.

FIGS. 26 and 27 will give an idea to the patient to watch for pressure loss. This can also be done by a plastic balloon having a mixture of air and water inside instead of the spring so that with pressure the air is compressed to allow the movement of the flat surface to occur and the measurement to be made.

Alternatively the unit can be connected to a presently available sphygmometers to have the pressure of the balloon to be measured, or a presently available device may be used for such purpose.

The Inner Wraps:

This is a wrap (FIG. 26) made from a soft, comfortable, absorbent material, such as clean and sterile cotton, that matches and fits the size and shape of the support unit and is slightly larger (due to the rims 285 and 286) to prevent the support unit from touching the bare skin. This inner cover is to give good feeling to the patient as well as providing sterility and cleanness to the area and the system. This unit will wrap around the patient and may have bands of adhesive film on it, in its rim, and different parts of the cover as desired. This film of adhesive is covered by a thin plastic layer that is removably stuck to it and will be removed at the time of use to allow the inner cover to be placed over the skin under the wrap. The rims of this cover can be turned outside to go over the edge of the support system to prevent it from hurting the skin of the patient. This inner cover may also have a thin plastic layer on its outside to prevent from leakage of blood to the pants and shirt, etc.

The Directions and General Informations About the Way this Unit Should Be Used:

Prior to application of this unit, the patient should not have an active bleeding at the site of surgery to give a chance for proper application of the unit.

First, when a patient is in supine position, the wrap, covered by the inner wrap, is placed under the patient in an appropriate position.

Second, the inner wrap is wrapped around the patient, and the place where the balloons will be placed is chosen.

Third, the balloons are placed on the appropriate positions. A layer of glue on the outer surface of the inner wrap may be used to hold the balloon in place reasonably secure.

Fourth, the ends of the lower straps or wraps are brought together and tightened to hold the balloon in place. Then the ends of the upper straps or wraps are tightened together. The balloons may be inflated to some degree prior to this stage to make the positioning easier.

Fifth, the balloons are inflated further to provide the desired pressure. At this stage their pressure may be checked and then the openings of the balloon closed. Then the patient is asked to move and sit on a chair and report if there is any problem. A measuring gauge and an inflator bulb or a syringe are provided to patients with explanation of how to use them if they happen to be needed and the telephone number to call if they have problems or questions.

This unit is applied in the hospital or clinic prior to discharge of the patient or when patient is being moved out of the bed.

I believe the use of this unit has the following distinct advantages:

1. Most importantly it is the best available way to prevent bleeding and complications in the intervention area. The protection will give the most and best peace of mind to the patient, their relatives, and the physicians.

2. It will prevent or diminish the complication in the area. I believe that many times the damage to the artery and the area is small and will not be detected or even when noted. Nothing really can be done or will be done about them due to the limitation of present techniques. However even if small, they are still bad, and the patients will suffer to one degree or another. This should be avoided by use of these units.

3. When the protection of the patient from bleeding can be continued by these units, then the patients can be discharged earlier from hospital and this has the great advantage to diminish the need for very skilled medical personnel to stay longer and to give longer care to these patients. This will diminish the cost and may pay for these units many times.

4. This will allow early discharge of the patient and it is good for the patient and his family. Some can be released during day time rather that being kept until dark. It may also help a patient to return to the job earlier.

5. The need for use of heavy adhesive taping and Tin co bin and gauzes will be practically eliminated, and this will also help the unit to be paid off.

6. When the use of adhesive tapes and Tin co bin is drastically diminished, then it will decrease the related allergic reaction and skin discomfort as well.

7. It is important to notice that the fact that the pressure inside the balloon can be changed by this given method gives is big, useful option, since the need for pressure can change due to different physical and pathological conditions of a patient (even in one case itself). For example the level of blood pressure of patient makes a big difference, or if a condition with cough develops that increases the need for more protection, or the weight of a patient and their body build, etc.

One further point concerning FIG. 17 is that 227 denotes a couple of bands of elastic that variably (the length to be adjustable) connect pieces 226 and 224 together at the sides.

What is claimed is:

1. A device for preventing bleeding from a wound proximate a person's groin line created as a consequence of catheterization of an underlying vessel, said device comprising first inflatable balloon means for disposition exclusively to one of the abdomen-side and the thigh-side of the groin line, second inflatable balloon means for disposition exclusively to the other of the abdomen-side and the thigh-side of the groin line, said first and second balloon means comprising respective edges proximate to and substantially parallel with the groin line, and a wrap for encircling the person comprising a frontal portion for placement over said first and second balloon means such that when said first and second balloon means are inflated, said wrap resists expansion of said first and second balloon means to exert pressure on the person, including exerting pressure on the wound, and in which said wrap comprises two separate straps, one encircling the abdomen, and the other encircling the thigh.

2. A device for preventing bleeding from a wound proximate a person's groin line created as a consequence of catheterization of an underlying vessel, said device comprising inflatable balloon means disposed inside of shorts to be worn by the person, and a wrap for encircling the person on the outside of said shorts comprising a frontal portion for placement over said balloon means such that when said balloon means is inflated, said wrap resists expansion of said balloon means to exert pressure on the wound, including attachment means for attaching said wrap to said shorts in the vicinity of said balloon means, and in which said wrap comprises two separate straps, one encircling the abdomen, and the other encircling the thigh.

3. A device as set forth in claim 2 including further attachment means for attaching said balloon means to said shorts.

4. A device for preventing bleeding from a wound proximate a person's groin line created as a consequence of catheterization of an underlying vessel, said device comprising inflatable balloon means disposed inside of shorts to be worn by the person, and a wrap for encircling the person on the outside of said shorts comprising a frontal portion for placement over said balloon means such that when said balloon means is inflated, said wrap resists expansion of said balloon means to exert pressure on the wound, in which said wrap comprises two separate straps, one encircling the abdomen and the other encircling the thigh.

* * * * *